United States Patent
Lisignoli et al.

(10) Patent No.: US 10,016,444 B2
(45) Date of Patent: Jul. 10, 2018

(54) MOLECULES FOR BONE TISSUE REGENERATION

(71) Applicants: ISTITUTO ORTOPEDICO RIZZOLI, Bologna (IT); UNIVERSITA' DI PISA, Pisa (IT)

(72) Inventors: Gina Lisignoli, Castello d'argile (IT); Francesco Grassi, San Lazzaro (IT); Vincenzo Calderone, Marina di Massa (IT); Simona Rapposelli, Capannori (IT)

(73) Assignees: ISTITUTO ORTOPEDICO RIZZOLI, Bologna (IT); UNIVERSITA' DI PISA, Pisa (IT)

( * ) Notice: Subject to any disclaimer, the term of this patent is extended or adjusted under 35 U.S.C. 154(b) by 0 days.

(21) Appl. No.: 15/524,257

(22) PCT Filed: Nov. 5, 2015

(86) PCT No.: PCT/IB2015/058551
§ 371 (c)(1),
(2) Date: May 3, 2017

(87) PCT Pub. No.: WO2016/071863
PCT Pub. Date: May 12, 2016

(65) Prior Publication Data
US 2017/0319605 A1 Nov. 9, 2017

(30) Foreign Application Priority Data
Nov. 7, 2014 (IT) .............. MI2014A1919

(51) Int. Cl.
C07C 331/28 (2006.01)
A61K 31/663 (2006.01)
C07C 331/24 (2006.01)
C07F 9/38 (2006.01)

(52) U.S. Cl.
CPC .......... *A61K 31/663* (2013.01); *C07C 331/24* (2013.01); *C07C 331/28* (2013.01); *C07F 9/38* (2013.01)

(58) Field of Classification Search
CPC .................. C07C 331/28; A61K 31/663
See application file for complete search history.

(56) References Cited

FOREIGN PATENT DOCUMENTS

| CN | 1333210 A | 1/2002 |
|---|---|---|
| WO | 2010083613 A1 | 7/2010 |

OTHER PUBLICATIONS

Xie et al. (Bioorg. Med. Chem. Lett, 15 (2005), p. 3267-3270).*
International Search Report and Written Opinion of PCT/IB2015/058551 dated Feb. 15, 2016.

* cited by examiner

*Primary Examiner* — Robert Havlin
(74) *Attorney, Agent, or Firm* — Silvia Salvadori, P.C.; Silvia Salvadori

(57) ABSTRACT

The invention relates to compounds of general formula (I) and pharmaceutically acceptable salts thereof: (I) wherein Ri is selected from an SCN— group or is an RCONH— group; in particular, where Ri=RCONH, R is selected from an aromatic benzene ring substituted with an SCN— group in the ortho, meta or para position, according to the following formula: SCN— or R is a C1-C4 alkyl chain, substituted with an SCN— group; n can be equal to 0 or else 1. The invention also relates to the use of such compounds for the treatment of osteoporosis and in general of bone pathologies characterized by a progressive loss of bone mass, for example rheumatoid arthritis, hyperparathyroidism or bone tumor metastases.

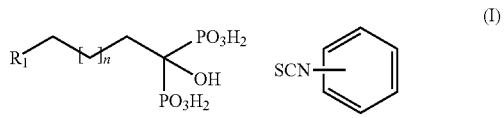

7 Claims, 8 Drawing Sheets

MOLECULES FOR BONE TISSUE REGENERATION

This application is a U.S. national stage of PCT/IB2015/058551 filed on 5 Nov. 2015 which claims priority to and the benefit of Italian Application No. MI2014A001919 filed on 7 Nov. 2014, the content of which are incorporated herein by reference in their entireties.

TECHNICAL FIELD

The present invention relates to new compounds for the treatment of osteoporosis and in general of bone pathologies characterised by a progressive loss of bone mass, for example rheumatoid arthritis, hyperparathyroidism or bone tumour metastases.

PRIOR ART

Osteoporosis represents one of the main causes of disability and morbidity in the world (Kanis J A et al. Osteoporos Int (2008) 19:399-428); among the many causes of osteoporosis, the decline in the physiological levels of estrogen that occurs in postmenopause continues to be the most frequent (Compston J. Best. Pract. Res. Clin. Rheumatol. 19, 1007-1009, 2005); still today, the pharmacological approach that is by far the most prevalent in the prevention and treatment of osteoporosis-induced bone fragility is represented by treatment with drugs inhibiting bone resorption, the function performed by osteoclasts (OC). The most successful family of drugs in this category are the bisphosphonates, developed in successive phases as chemical analogues of pyrophosphates, well-known inhibitors of mineralisation. FIG. 1 shows the structural formula of the main bisphosphonates presently used in the treatment of osteoporosis.

However, this mechanism does not reconstitute the bone mass already lost (Delmas, P D, Lancet (2002), 359, 2018-2023). Moreover, the inhibition of the action of osteoclasts results in a prolonged suppression of the physiological mechanisms that control bone turnover, with a possible consequent increase in bone fragility due to the simultaneous suppression of bone neoformation associated with the 'coupling' effect. This has given rise to a strong increase in scientific and clinical interest in drugs capable of stimulating the anabolic function of bone instead of suppressing it (Martin T J and Seeman E., Clinical Science (2007), 112, 77-91), or of combining a moderate anti-catabolic action with an anabolic one in such a way as to stimulate the physiological mechanisms of bone turnover rather than inhibiting them.

Hydrogen sulphide ($H_2S$) is a gaseous molecule historically known as a toxic agent. However, in recent years, an important biological role has been attributed to $H_2S$, which is physiologically produced by cells in minimal quantities and performs a gas transmitting function, comparable to that of molecules that have been studied for a long time, such as nitric oxide or carbon oxide. The main effects of $H_2S$ on cells and tissues include cytoprotective, antioxidant, anti-inflammatory effects and induction of vasodilation (Kimura H., Antioxidant & Redox Signaling, 2014 Feb. 10; 20(5): 783-93; Yang G. et al, Science, 2008 Oct. 24; 322(5901): 587-90). The Applicants realised, through preliminary studies, that $H_2S$ is able to significantly modulate the function and phenotypic differentiation of human bone cells. Bone tissue is highly dynamic and undergoes constant remodelling also during adult life; a finely regulated process, known as 'coupling', continuously maintains a balance in the degradation (or resorption) of mineral bone tissue, carried out by osteoclasts, with the formation of new bone tissue carried out by osteoblasts within microscopic functional units located at the interface between the bone and bone marrow (Hattner R. et al. Nature 1965; 206(983):489-90). When the degradation of bone tissue is no longer balanced by formation, as occurs in pathological conditions such as osteoporosis, there is a net loss of bone tissue, which dramatically increases the risk of fractures. Preliminary experiments have suggested that $H_2S$ functions by stimulating mesenchymal stem cells (MSCs), the precursors of osteoblasts, thereby inducing an increase in the deposition of new bone mineral matrix.

Based on these considerations, the Applicants have concentrated on developing a new class of molecules that could act as hybrid drugs—drugs capable, that is, of combining the properties of a known drug for osteoporosis, alendronate, with those of a functional group capable of releasing $H_2S$.

The molecules of the invention thus address this pressing clinical need, i.e. the need to develop new drugs capable of stimulating the physiological mechanisms of bone turnover rather than inhibiting them, and which are thus useful in the treatment of osteoporosis. The molecules of the invention have been developed with the aim of coupling the anti-catabolic function of alendronate (due to the pyrophosphate groups) with an anabolic function due to $H_2S$.

SUMMARY OF THE INVENTION

The present invention relates to compounds of general formula (I), as shown below, pharmaceutically acceptable salts thereof, and the use thereof in the prevention and treatment of osteoporosis and in general of bone pathologies characterised by a progressive loss of bone mass, for example rheumatoid arthritis, hyperparathyroidism or bone tumour metastases.

The compounds of the invention have the following general formula:

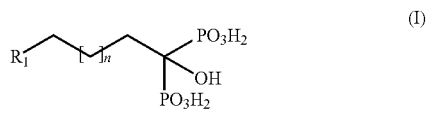

wherein $R_1$ is selected from an SCN— group or an RCONH— group; in particular, where R1=RCONH, R is selected from an aromatic benzene ring substituted with an SCN— group in the ortho, meta or para position, according to the following formula:

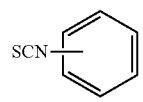

or R is a C1-C4 alkyl chain, substituted with an SCN— group;
n can be equal to 0 or 1.

DETAILED DESCRIPTION OF THE INVENTION

Figure 1:
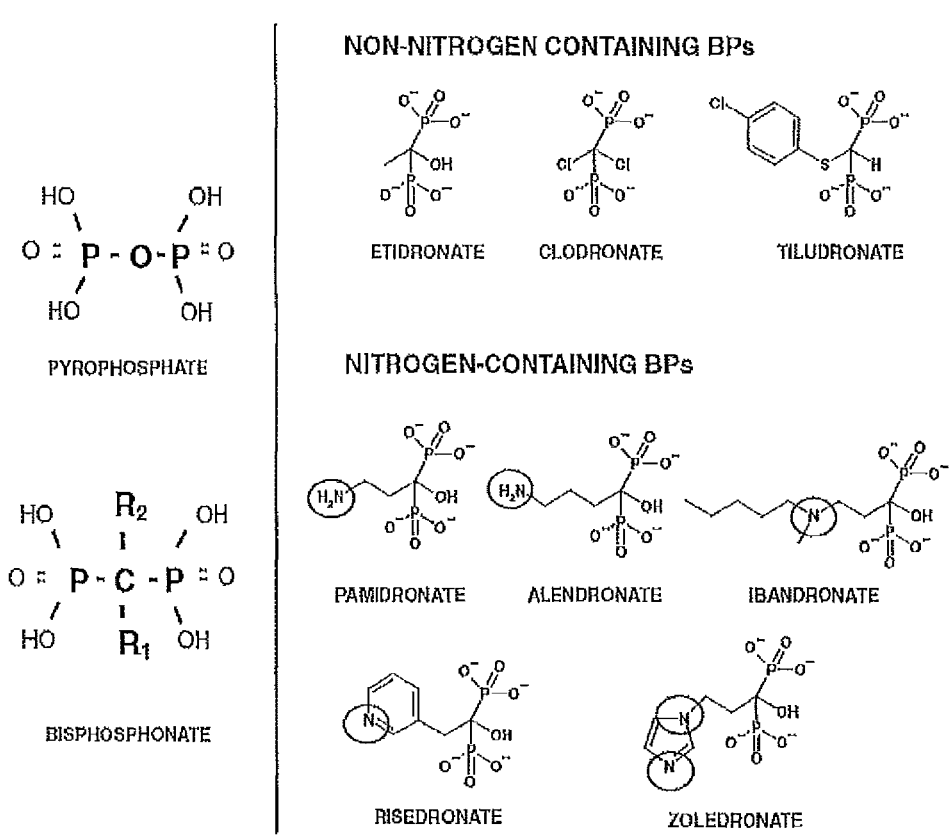
FIG. 1 shows the structural formula of the main bisphosphonates presently used in the treatment of the osteoporosis.

"Pharmaceutically acceptable salts" of the compounds of formula (I) means alkali or alkaline earth metals, for example sodium salt, organic bases such as alkyl amine salts (ethyl amine, diethyl amine, ethylene diamine and amino ethanol) or basic amino acids such as lysine salt. The present invention relates to compounds of general formula (I) and pharmaceutically acceptable salts thereof:

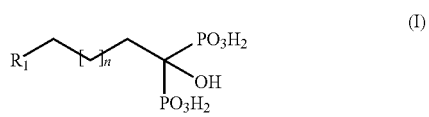

wherein $R_1$ is selected from an SCN— group or is an RCONH— group; in particular, where R1=RCONH, R is selected from an aromatic benzene ring substituted with an SCN— group in the ortho, meta or para position, according to the following formula:

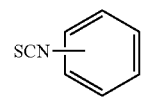

or else R is an alkyl chain C1-C4, substituted with an SCN— group;

n can be equal to 0 or 1.

Preferably, R1 is an RCONH— group. More preferably, R1 is an RCONH— group and R is a benzene ring substituted with an SCN— group in the ortho, meta or para position.

Preferably, R is a benzene ring substituted with an SCN— group in the ortho, meta or para position. More preferably, the substitution of the SCN— group is in the para position.

When R is an alkyl chain substituted with the SCN— group, the alkyl chain is preferably a C3 or C4 chain. Preferably, the substitution of the SCN— group is a substitution at the C-terminal of the alkyl chain.

In one embodiment of the invention, R is a benzene ring ortho-, meta- or para-substituted with an SCN— group and n is equal to 1.

In a preferred embodiment, R is a benzene ring para-substituted with an SCN— group and n is equal to 1.

In a particularly preferred embodiment of the invention, the compound of formula (I) is (1-hydroxy-4-{[(4-phenyl isothiocyanate)carbonyl]amino}butane-1,1-bisphosphonic acid, according to the following structural formula:

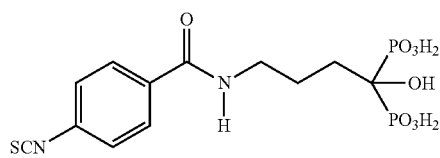

The invention also relates to the use of compounds of formula (I) or pharmaceutically acceptable salts thereof as a medicament.

In particular, the compounds of formula (I) or pharmaceutically acceptable salts thereof are used for the prevention and treatment of osteoporosis and in general of bone pathologies characterised by a progressive loss of bone mass, for example rheumatoid arthritis, hyperparathyroidism or bone tumour metastases.

In a further aspect, the invention relates to a method for treating osteoporosis, rheumatoid arthritis, hyperparathyroidism or bone tumour metastases, which comprises administering an effective dose of a compound of formula (I) or of a pharmaceutically acceptable salt thereof to a patient affected by that pathology.

The doses and concentrations of administration of the compounds of formula (I) are selected each time by a physician based on the patient's needs.

The molecules of formula (I) combine the osteoanabolic effects of $H_2S$, already observed in numerous preliminary experiments conducted by the Applicants, with the anti-catabolic effects of alendronate, one of the molecules most widely used in pharmacology for erosive bone pathologies. In recent years this drug, despite its great commercial success, has shown some negative side effects, essentially ascribable to an excessive suppression of the cellular functionality of OCs and osteoblasts alike.

The compounds of the invention thus aim to meet the most pressing needs of pre-clinical research on this type of pathologies: to develop new molecules capable of combining an anti-catabolic effect with one of an anabolic type, such as to favour, rather than suppress, the physiology regulating normal bone turnover.

The tests included here also demonstrate a positive profile of the compounds of formula (I) from a toxicity standpoint. In particular, (1-hydroxy-4-{[(4-phenylisothiocyanate)carbonyl]amino}butane-1,1-bisphosphonic acid, in the range of concentrations tested, demonstrates to be a more cytoprotective and nontoxic molecule compared to the native molecule alendronate, which, by contrast, in agreement with the data in the literature and with clinical evidence, tends to induce cell death in MSCs.

As regards the data related to the modulation of cellular functionality, (1-hydroxy-4-{[(4-phenylisothiocyanate)carbonyl]amino}butane-1,1-bisphosphonic acid has first of all demonstrated to be capable of promoting the ability of MSC cells to deposit mineral matrix; this assay represents a reliable experimental model for predicting the ability of cells in vivo to perform an osteoanabolic function in bone tissue. The results show an outcome of great relevance, given that not only does (1-hydroxy-4-{[(4-phenylisothiocyanate)carbonyl]amino}butane-1,1-bisphosphonic acid provide better results than alendronate in each of the tested concentrations, but it also shows, in absolute terms, an induction of the deposition of bone matrix by MSC cells, as compared to control cells induced to osteogenic differentiation.

The potential pharmacological impact of the data on MSC cells is even further reinforced by the data obtained on OCs, which were analysed in order to verify the anti-catabolic effects of the compounds of the invention. They show, in fact, that (1-hydroxy-4-{[(4-phenyl isothiocyanate)carbonyl]amino}butane-1,1-bisphosphonic acid maintains the ability to inhibit the differentiation and function of OCs, a property typical of alendronate, but attenuates the effectiveness thereof, making higher dosages necessary in order to reach a similar level of inhibition. In consideration of the fact that alendronate has a very long half-life and shows a marked tendency to accumulate in bone mineral matrix, the data on (1-hydroxy-4-{[(4-phenylisothiocyanate)carbonyl]amino}butane-1,1-bisphosphonic acid suggest overall that this molecule may have a much more balanced effect than alendronate on bone cells; on the one hand, in fact, (1-hydroxy-4-{[(4-phenylisothiocyanate)carbonyl]amino}butane-1,1-bisphosphonic acid remains capable in any case of blocking the function of OCs, but as it requires a greater concentration, it could exert a moderate rather than radical suppression of OC function. On the other hand, (1-hydroxy-4-{[(4-phenylisothiocyanate)carbonyl]amino}butane-1,1-bisphosphonic acid is able to induce, in the same range of concentrations in which it inhibits OCs, a significant function of stimulating mineralisation by human MSCs.

In summary, the compounds of formula (I) possess the following unexpected and innovative properties:
- the compounds of formula (I) constitute a new class of compounds with an original and innovative chemical structure;
- the compounds of formula (I) are capable of liberating $H_2S$ with slow-release kinetics;
- Concentrations being equal, (1-hydroxy-4-{[(4-phenyl isothiocyanate)carbonyl]amino}butane-1,1-bisphosphonic acid shows no cytotoxicity and is cytoprotective compared to the 'mother' molecule alendronate. Furthermore, within the limit of 24 h of culture, it is cytoprotective also in absolute terms compared to the unstimulated control;
- the compounds of formula (I) do not modify the proliferative capacity of MSCs, whereas alendronate provokes a marked decrease;
- the compounds of formula (I) induce a significant increase in mineralisation in human osteoprogenitor cells, thus exerting an osteoanabolic function;
- in the same concentration range in which it stimulates the anabolic function (10-33 µM), (1-hydroxy-4-{[(4-phenyl isothiocyanate)carbonyl]amino}butane-1,1-bisphosphonic acid significantly inhibits the differentiation and bone degradation function of osteoclasts;
- Concentrations being equal, (1-hydroxy-4-{[(4-phenyl isothiocyanate)carbonyl]amino}butane-1,1-bisphosphonic acid is approximately 33-100 times less effective than alendronate in suppressing OCs, thus suggesting an effect of moderate suppression which maintains the homeostatic function of the OCs themselves intact without causing the total inhibition typical of alendronate.

The compounds of formula (I) are synthesized following the synthesis scheme illustrated in the experimental part.

EXPERIMENTAL PART

The code DM-22 indicates (1-hydroxy-4-{[(4-phenyl isothiocyanate)carbonyl]amino}butane-1,1-bisphosphonic acid.

Synthesis

Synthesis of 4-{[(4-nitrophenyl)carbonyl]amino}butanoic acid

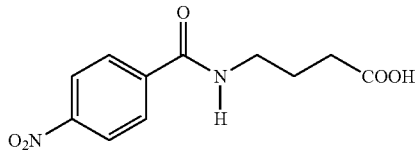 [SMILES: O=C(O)CCCNC(=O)c1ccc([N+](=O)[O-])cc1]

P-nitrobenzoic acid (300 mg; 1.64 mmol) was treated with $SOCl_2$ (685 mg; 5.76 mmol) at 80° C. for 12 h. The solvent was evaporated to obtain a yellow solid which was dissolved in the minimum quantity of THF and added dropwise to a solution of γ-aminobutyric acid (78 mg; 0.76 mmol) in NaOH aq (156 mg, 4.40 ml) maintained at 5° C. The resulting solution was left to stir at room temperature for 12 h; it was then acidified to pH 2 with an aqueous solution of HCl 1 N. The precipitate was collected and crystallized from H₂O so as to obtain a white solid corresponding to the desired product (197 mg, 0.78 mmol; yield 74%).

NMR (CD3OD): δ 1.86-2.00 (m, 2H, CH₂); 2.41 (t, 2H, J=7.3 Hz, CH₂); 3.46 (t, 2H, J=6.9 Hz, CH₂); 8.02 (d, 2H, J=9.0 Hz, Ar); 8.32 (d, 2H, J=9.0 Hz, Ar) ppm.

Synthesis of 4-{[(4-aminophenyl)carbonyl]amino}butanoic acid

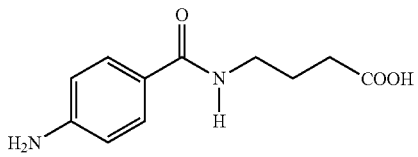

Carbon (16 mg) and FeCl₃ (catalytic amount) were added to a solution of 4-{[(4-nitrophenyl)carbonyl]amino}butanoic acid (77 mg; 0.31 mmol) in MeOH (2 ml), under a flow of N₂. H₂NNH₂.H₂O (116 mg; 5.18 mmol) was added after 5 min. under reflux and heating was continued for 24 h. After this time, the reaction mixture was filtered through celite and the solvent evaporated to obtain a crude product that was purified by precipitation from EtOH/Et₂O (43 mg; 0.19 mmol; yield 64%).

NMR (CD₃OD): δ 1.80-1.94 (m, 2H, CH₂); 2.28 (t, 2H, J=7.2 Hz, CH₂); 3.37 (t, 2H, J=6.8 Hz, CH₂); 6.66 (d, 2H, J=8.5 Hz, Ar); 7.60 (d, 2H, J=8.5 Hz, Ar) ppm.

Synthesis of 4-{[(4-aminophenyl)carbonyl]amino}-1-hydroxybutane-1,1-bis-phosphonic acid

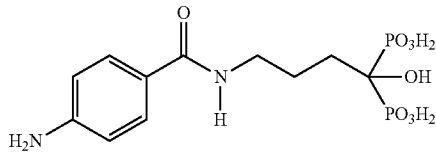

A solution of catecholborane (1M in THF; 0.88 ml; 0.88 mmol) was added to 4-{[(4-aminophenyl)carbonyl]amino}butanoic acid (63 mg; 0.28 mmol), under a flow of nitrogen. The reaction mixture was left to stir at room temperature for 1 h until the formation of H₂ was no longer observed. Then P(OSiMe₃)₃ (347 mg; 1.16 mmol) was added, and stirring was continued for 16 h at room temperature. MeOH (1 ml) was subsequently added to the solution, which was left to stir for an additional hour. The solvent was then evaporated and CHCl₃ was added to the residue until an oil formed; the oil was precipitated from MeOH/Et₂O (73 mg; 0.20 mmol; yield 70%).

NMR (D₂O): δ 1.85-2.44 (m, 4H, CH₂); 3.40 (t, 2H, J=6.6 Hz, CH₂); 7.47 (d, 2H, J=8.7 Hz, Ar); 7.82 (d, 2H, J=8.7 Hz, Ar); 8.41 (s, 2H, NH₂) ppm.

Synthesis of (1-hydroxy-4-{[(4-isothiocyanate phenyl)carbonyl]amino}butane-1,1-bis-phosphonic acid

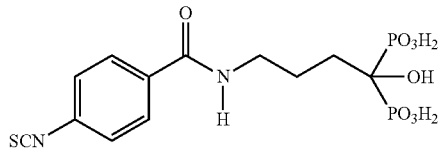

Triphosgene (228 mg; 1.98 mmol) was added to a solution of 4-{[(4-aminophenyl)carbonyl]amino}-1-hydroxybutane-1,1-bis-phosphonic acid (73 mg; 0.20 mmol) in NaHCO₃ (0.4 M in H₂O; 2 ml). The reaction mixture was left to stir at room temperature for 2 h and was then extracted with CH₂Cl₂. The organic phase was reduced in volume and precipitated with hexane so as to obtain an oil corresponding to the desired product (20 mg; 0.048 mmol; yield 24%).

NMR (CD₃OD): δ 1.84-1.98 (m, 2H, CH₂); 2.39 (t, 2H, J=7.3 Hz, CH₂); 3.42 (t, 2H, J=6.8 Hz, CH₂); 7.36 (d, 2H, J=8.4 Hz, Ar); 7.86 (d, 2H, J=8.4 Hz, Ar) ppm.

¹H NMR (400 MHz, D₂O): δ1.90-2.15 (m, 4H, CH₂); 3.45 (t, J=6.6 Hz, 2H, CH₂); 7.43 (d, J=8.8 Hz, 2H, Ar); 7.80 (d, J=8.8 Hz, 2H, Ar) ppm.

¹³C NMR (400 MHz, D₂O): δ 167.70, 129.37, 128.93, 126.39, 124.06, 123.70, 76.66, 40.56, 31.24, 23.52 ppm.

³¹P NMR (400 MHz, D₂O): δ 19.23 ppm.

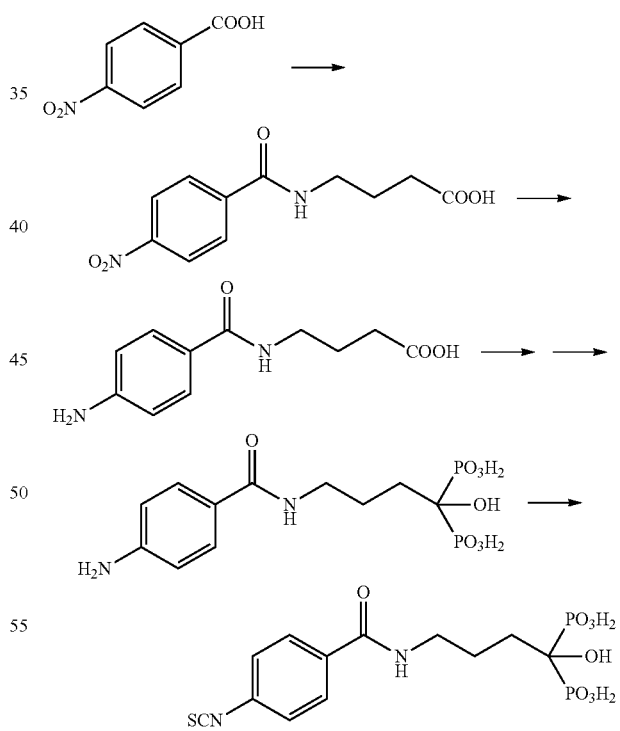

Determination of the Release of H₂S by DM-22

Amperometry—the potential release of H₂S from the tested compound was evaluated by means of the amperometric method, using an Apollo-4000 Free Radical Analyzer (WPI) connected to mini-electrodes selective for H₂S. The experiments were conducted at room temperature in phosphate buffer (NaH₂PO₄.H₂O 0.128 g, Na₂HPO₄.12H₂O 0.597 g, NaCl 4.388 g in 500 mL H$_2$O) at pH 7.4. When required by the experimental protocol, 4 mM L-cysteine was also dissolved in the above-described phosphate buffer, maintaining the pH a 7.4. After stabilisation of the mini-electrodes selective for H$_2$S in 10 mL of buffer, 100 µL of the compound DM-22 solubilised in DMSO was added at the final concentration of 1 mM. The formation of H$_2$S was recorded for 20 minutes. The same experimental procedure was also carried out in the buffer containing L-cysteine. The correspondence between the amperometric currents (recorded in pA) and the concentrations of H$_2$S was determined by means of suitable calibration curves previously obtained using increasing concentrations of NaHS (1 µM, 3 µM, 5 µM, 10 µM) at pH 4.

The curves related to the progressive release of H$_2$S as a function of time were analysed by means of the following equation:

$$Ct = Cmax - (Cmax \cdot e - k \cdot t)$$

Where Ct is the concentration at time t, Cmax is the maximum concentration obtained during the recording time and the constant k is 0.693/t½, and where t½ is the time it takes to reach half of Cmax. The values of Cmax and t½ were calculated by means of software: Graph Pad Prism 4.0 and expressed as a value±standard error.

Isolation of Human Mesenchymal Stem Cells (MSCs).

Human MSCs were obtained according to an already published method (Lisignoli G. et al. J Cell Physiol, 2009). Briefly, 5 ml of bone marrow aspirate was obtained from consenting patients who underwent post-traumatic orthopaedic surgery. The mononuclear cells were obtained following centrifugation in a density gradient (Ficoll-Hypaque); the cells thus obtained were washed with PBS, resuspended in a D-MEM culture medium containing 15% FBS, then counted and seeded in plastic flasks at a concentration of 2×106 cells/flask T150. After 1 week, the non-adherent cells were removed and the adherent cells expanded in culture up to the concentration of 5000 MSC/cm$^2$ and used, finally, in the culture passage p.1 for the experiments.

Analysis of Cell Proliferation.

Cell proliferation was measured in the MSCs by means of the tritiated thymidine method, in the presence or absence of stimuli, following a method already published in precedence (Gabusi E. et al. J Cell Physiol. 2011). Briefly, the cells were seeded in triplicate at a density of 5×103/well in 96-well plates and stimulated with DM-22 or alendronate, in the range of concentrations comprised between 1 and 33 µM. After 48 h, tritiated thymidine (Amersham Pharmacia Biotech Italy, Milan) was added to each well at the final concentration of 2 mCi/ml and the culture further incubated for 18 h at 37° C. Lastly, the plates were aspirated through glass fibre filters and dried and the radioactivity incorporated in the cells, indicative of proliferative activity, was measured by means of a TopCount Microplate Scintillation Counter (Packard Instrument Company, Meriden, Conn.). The data are expressed as cpm (count per minute).

Analysis of Cytotoxicity.

For the cytotoxicity analysis the MSCs were seeded in triplicate at the density of 1×104/well in 48-well plates and stimulated with DM-22 or alendronate in the range of concentrations comprised between 1 and 33 µM. Cytotoxicity was evaluated in the culture after 24 h and 72 h by means of the lactate dehydrogenase (LDH) method, using a commercial kit (Cytotoxicity Detection Kit, Roche, Milan). In order to avoid interferences due to components present in serum, the cells were maintained under low serum conditions (5%) in the culture medium.

At the end of the period of culture, moreover, the MSCs underwent staining with Toluidine Blue stain in order to evaluate the residual viability, which was then quantified by means of a spectrophotometer (Nanoquant, Tecan Group, Mannedorf, Switzerland).

Mineralisation Assay.

The evaluation of the functional capacity to deposit inorganic matrix on the part of MSC cells was evaluated with an in vitro mineralisation assay, according to an already consolidated method (Grassi F. et al. J. Tissue Eng Reg Med, 2013); MSC cells were maintained under culture for 21 days in the presence of 100 mM of ascorbic acid, 2 mM of β-glycerophosphate and 100 nM of dexamethasone. The medium was changed twice a week with the addition of DM-22 or alendronate at the specified concentrations. Finally, the mineralised matrix was visualised by staining with Alizarin Red and quantified by spectrophotometry (Nanoquant, Tecan Group, Mannedorf, Switzerland).

Differentiation of Human Osteoclasts

Human osteoclasts (OCs) were obtained according to a method already described and published (Grassi F. et al. J Cell Physiology 2011 April; 226(4):982-90). Briefly, the OCs were differentiated in vitro starting from monocytic precursors obtained from the peripheral blood of healthy, consenting donors; in particular, whole blood was stratified on Ficoll-Hypaque and the mononuclear cells were obtained by centrifugation. Monocytes were isolated from the latter by immunomagnetic separation of cells positive to the antigen CD11b via a MACS apparatus (Miltenyi Biotech, Calderara di Reno, Bologna). The cells thus obtained were collected, washed with PBS and seeded at a density of 2×106 cells/mL in the presence of M-CSF (Miltenyi Biotech, 10 ng/ml) and RANKL (Miltenyi Biotech, 75 ng/ml) for 8 days in the presence or absence of DM-22 or alendronate. The number of mature OCs obtained for each condition of stimulation was then identified by means of a manual count, under a microscope, of the multinuclear cells positive to tartrate-resistant acid phosphatase (TRAP) staining.

Assay for osteoclast functionality (Pit Assay).

The ability of OCs to perform a physiological function of degrading the inorganic matrix was assessed by means of the 'Pit Assay', in which the OCs were cultured on Biocoat Osteologic (BD Bioscience) slides according to the procedure described in detail above. On this substrate, mature OCs produce the characteristic pits, which were qualitatively assessed in order to compare the treatments with DM-22 vs. alendronate.

Statistical Analysis.

The data were analysed using the ANOVA method for non-parametric data, followed by a Wilcoxon post-hoc test. Comparisons were made between pairs of data using the T-Test. Data with p<0.05 were considered significant. The data shown represent the mean±standard deviation of 5 independent experiments.

Results

Kinetics of the Release of H$_2$S by DM-22.

Figure 2:
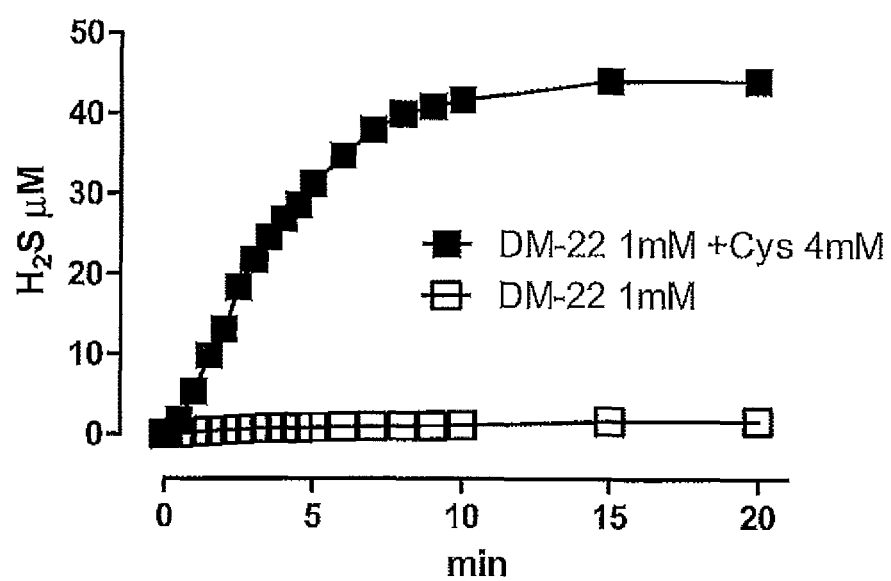
FIG. 2 illustrates the increase in the concentration of $H_2S$ detected after incubation of 1 mM (1-hydroxy-4-{[(4-phenyl isothiocyanate)carbonyl]amino}butane-1,1-bisphosphonic acid (DM-22) in phosphate buffer (white squares), and the increase in the concentration of $H_2S$ detected after incubation of the 1 mM acid in phosphate buffer in the presence of 4 mM L-cysteine (black squares)

As illustrated in FIG. 2, the incubation of 1 mM of DM-22 in phosphate buffer led to a slow, modest liberation of H$_2$S. The concentration of H$_2$S detected after 20 minutes of incubation was approximately 1.5 µM.

In accordance with the recently reported H$_2$S-donor properties of the isothiocyanate functional group (Martelli et al., ACS Med Chem Lett. 2013 Aug. 8; 4(10):904-8), the incubation of 1 mM DM-22 in phosphate buffer in the presence of 4 mM L-cysteine led to a gradual and significant liberation of H$_2$S. The maximum concentration of H$_2$S detected after 20 minutes of incubation was equal to approximately 45 µM, with a t½ of about 3 minutes. The results indicate, therefore, that DM-22 can be considered a compound capable of liberating $H_2S$ in the presence of organic thiols such as L-cysteine.

The graph in FIG. 2 illustrates the increase in the concentration of $H_2S$ detected after incubation of 1 mM DM-22 in phosphate buffer (white squares), and the increase in the concentration of $H_2S$ detected after incubation of 1 mM DM-22 in phosphate buffer in the presence of 4 mM L-cysteine (black squares).

Effect of DM-22 on MSCs: Viability and Proliferation.

Figure 3:
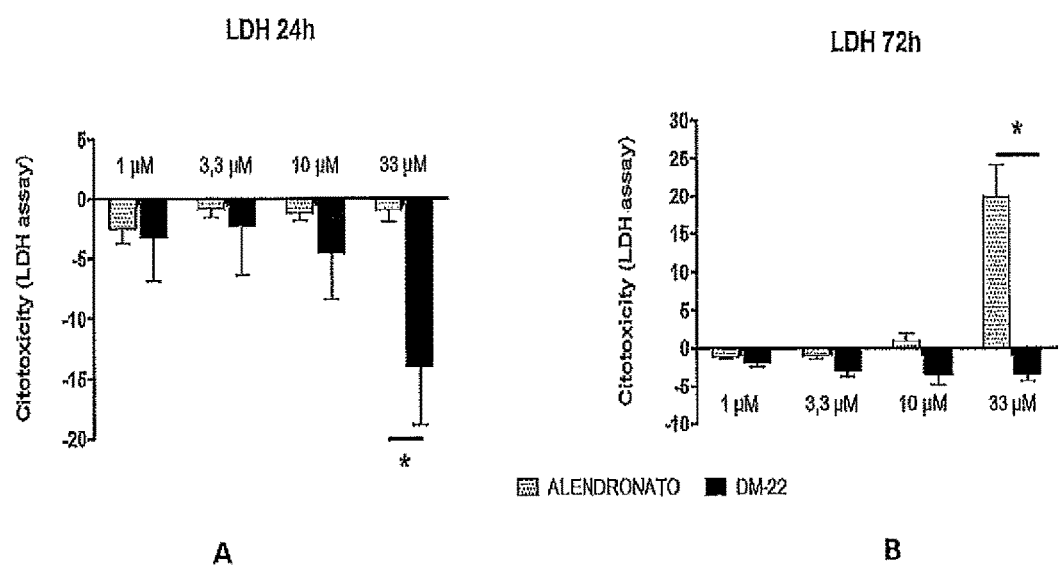
FIG. 3 shows the results of the cellular toxicity tests on MSC cells after stimulation with different concentrations of alendronate or DM-22; the graph shows the pattern of cytocellular toxicity following stimulation for 24 h (A) or 72 h (B) with DM-22 or alendronate; the graph expresses the level of cytotoxicity compared to unstimulated control samples. *=p<0.05.

The data obtained via the LDH assay indicate that the treatment with DM-22, at both 24 h and 72 h, does not induce any cytotoxicity (FIG. 3). In particular, at 24 h the treatment with DM-22 induces a significant protection compared to the basal level of cytotoxicity, induced in this assay by serum deprivation; at 72 h, on the other hand, consistently with the data present in the literature, the 33 µM concentration of alendronate induces a significant cellular toxicity, which is by contrast completely absent in the treatment with an analogous concentration of DM-22.

FIG. 3 shows the results of the cellular toxicity test on MSCs following stimulation with different concentrations of alendronate or DM-22. The graph shows the pattern of cytocellular toxicity following stimulation for 24 h (A) or 72 h (B) with DM-22 or alendronate. The graph expresses the level of cytotoxicity compared to the unstimulated control samples. *=p<0.05.

Consistently with the cytotoxicity data, cell viability, evaluated by staining with Toluidine Blue vital stain, confirmed that whereas the higher concentration of alendronate (33 µM) induces a significant decrease in cell viability (FIG. 4 A-B), DM-22 does not bring about any decrease as compared to the unstimulated control. Taken together, these data suggest that, in the experimental test conditions, the molecule DM-22 shows a better safety profile than alendronate, since not only does it not induce any toxicity or loss of cell viability, but under some conditions it has also shown cytoprotective effects.

Figure 4:
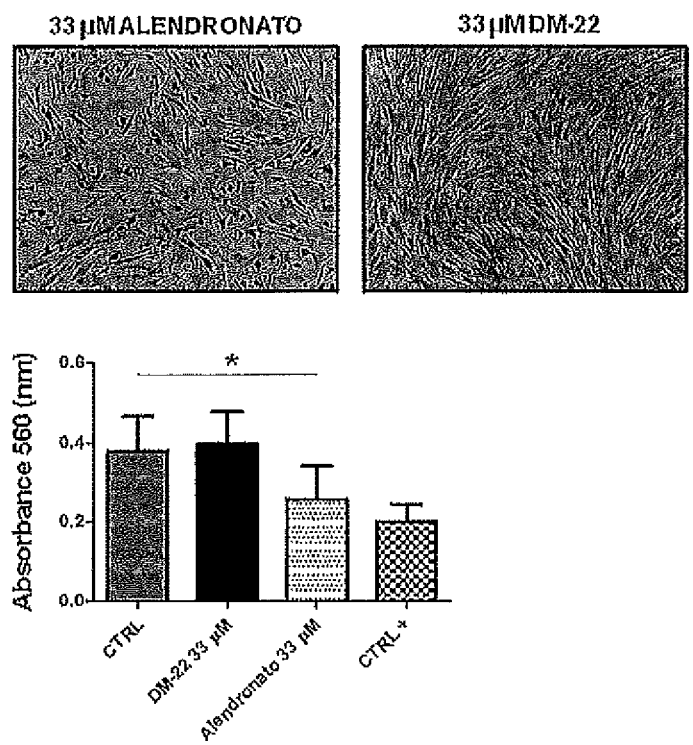
FIG. 4 shows the results of the cell viability tests on MSC cells after stimulation with alendronate or DM-22. The cells were maintained under culture for 72 h before being stained with Toluidine Blue and quantified; A: photos representing Toluidine Blue staining performed on MSCs treated with the 33 μM concentrations of the two reagents; B: quantification of staining in 5 independent experiments; the CTR+ sample represents the positive control obtained by inducing cellular toxicity with Triton X-100. *=p<0.05.

FIG. 4 shows the results of the cell viability test on MSCs after stimulation with alendronate or DM-22. The cells were maintained under culture for 72 h before being stained with Toluidine Blue and quantified. A: photo illustrating Toluidine Blue staining carried out on MSCs treated with the 33 µM concentrations of the two reagents. B: quantification of staining in 5 independent experiments; the CTR+ sample represents the positive control obtained by inducing cellular toxicity with Triton X-100. *=p<0.05.

Figure 5:
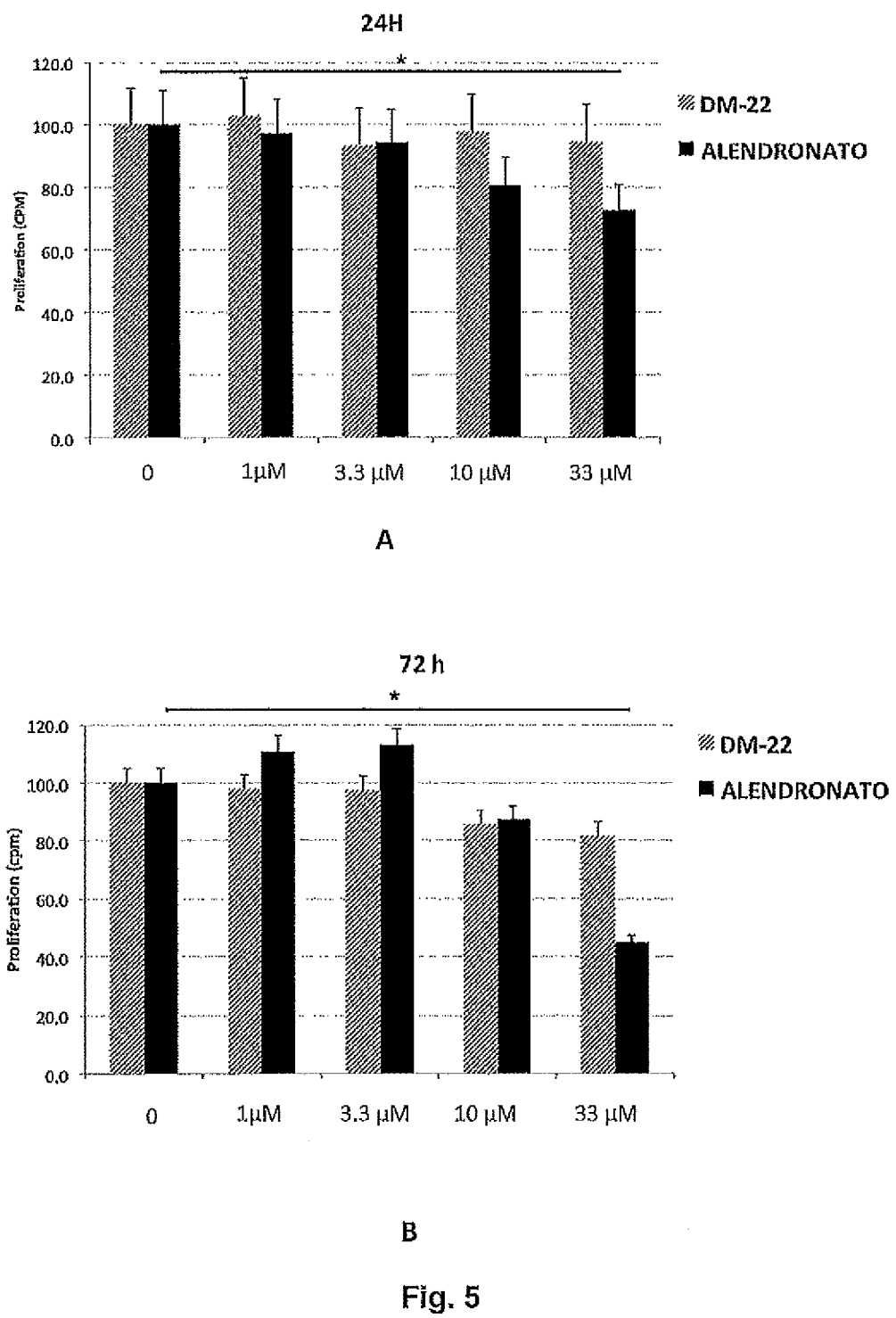
FIG. 5 shows the results of the cell proliferation tests on MSC cells after stimulation with different concentrations of alendronate or DM-22; the cells were maintained under culture for 24 or 72 h in the presence of the stimuli indicated; A: cell proliferation after 24 h of culture; B: cell proliferation after 72 h of culture; the data express the variation in proliferation relative to the unstimulated control (=100). *=p<0.05 vs. unstimulated.

In order to further test the ability of the two drugs to induce or inhibit a proliferative response in MSC cells, we performed a cell proliferation test with a protocol consistent with the one already used for the viability and cytotoxicity tests. Similarly to what was found with respect to viability and cellular toxicity, the 33 µM concentration of alendronate induces a significant inhibition of proliferative activity in MSCs, both at 24 and 72 h after stimulation (FIG. 5). An analogous concentration of DM-22, by contrast, does not induce any significant decrease in proliferation.

FIG. 5 shows the results of the test on MSC proliferation after stimulation with different concentrations of alendronate or DM-22. The cells were maintained under culture for 24 or 72 h in the presence of the stimuli indicated. A: cell proliferation after 24 h of culture. B: cell proliferation after 72 h of culture; the data express the variation in proliferation versus the unstimulated control (=100). *=p<0.05 vs unstimulated.

Effect of DM-22 on MSCs: Mineralisation Functional Assays.

Figure 6:
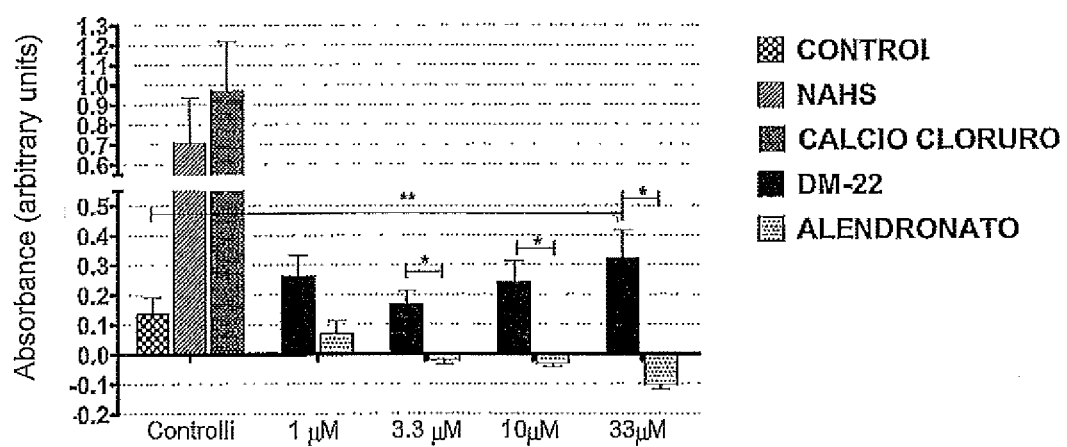
FIG. 6 shows the results of the mineralisation assay on MSC cells after stimulation with different concentrations of alendronate or DM-22; the cells were maintained under culture in osteogenic conditions for 21 days in the presence of the stimuli indicated; the data express the spectrophotometric quantification of staining performed with Alizarin Red at the end of the culture (=100); NaHS and Calcium chloride represent positive controls in this assay. *=p<0.05.

In order to better understand the ability of DM-22 to modulate the physiological function of MSCs, we investigated its effect during a mineralisation assay, in which the MSCs were induced to differentiate in an osteogenic direction so as to deposit an inorganic mineral matrix, in a manner that is similar to what takes place in bone tissue. As shown in FIG. 6, MSC cells mineralise under basal conditions (control) and respond as expected to noted osteogenesis stimulators such as NaHS and calcium chloride. Stimulation with alendronate induces a progressive, dose-dependent inhibition of their mineralising capacity, which may also be ascribed to the evident cytotoxicity highlighted previously. DM-22, by contrast, demonstrated a dose-dependent capacity to induce mineralisation; at the concentrations of 3.3, 10 and 33 µM it showed a significantly greater mineralisation than MSCs treated with alendronate. Even more importantly, at the maximum concentration of 33 µM, the degree of mineralisation induced by stimulation with DM-22 was significantly greater than that of the control MSCs. These data demonstrate that not only does DM-22 completely prevent the loss in mineralisation capacity induced by alendronate, but it also possesses a stimulation capacity in absolute terms, as compared to untreated MSCs, which thus indicates an osteoanabolic capacity.

FIG. 6 shows the results of the mineralisation assay on MSCs after stimulation with alendronate or DM-22. The cells were maintained under culture in osteogenic conditions for 21 days in the presence of the stimuli indicated. The data express the spectrophotometric quantification of staining with Alizarin Red at the end of the culture (=100). NaHS and Calcium chloride represent positive controls in this assay. *=p<0.05.

Effect of DM-22 on Osteoclast Differentiation and Function.

Figure 7:
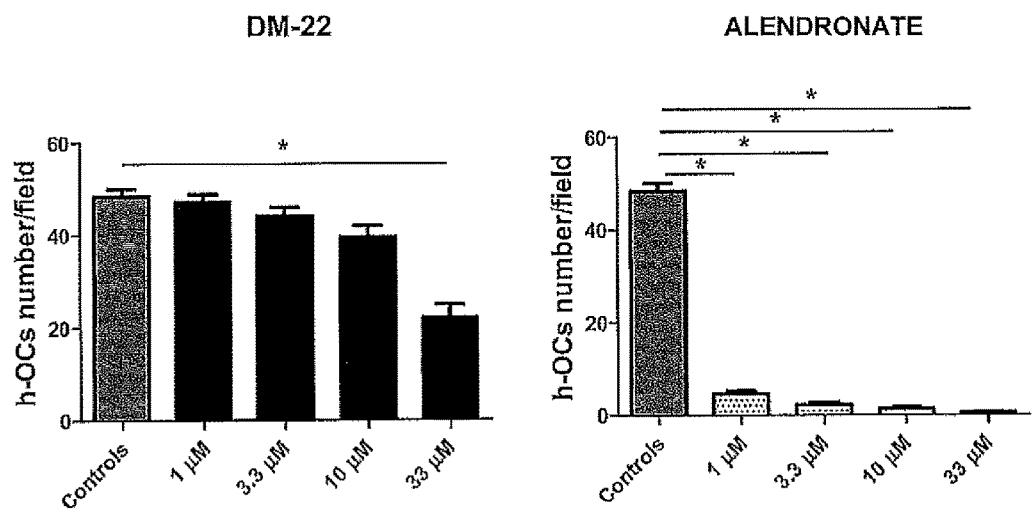
FIG. 7 shows the results of an OC differentiation assay. The OCs were obtained by differentiation of monocyte precursors in the presence of the specified concentrations of DM-22 or alendronate; the graphs indicate the number of mature OCs, identified as positive to TRAP staining and expressed as number of OCs per visual field at the end of culture. *=p<0.05.

Lastly, in light of the effects observed in MSCs, we tested DM-22 for its ability to exert an inhibitory effect against OCs, an effect typical of the native molecule alendronate. Cultures of OCs were stimulated with the two drugs and an assessment was made of the effects both on maturation of the OCs and their functionality. As shown in FIG. 7, and consistently with the literature, alendronate showed a strong capacity to inhibit OC differentiation starting from the lowest concentration used in the study (1 µM). The molecule DM-22 likewise demonstrated a capacity to inhibit OC differentiation, but the effect is statistically significant only at the highest concentration (33 µM).

FIG. 7 shows the results of an OC differentiation assay. The OCs were obtained by differentiation of monocyte precursors in the presence of the specified concentrations of DM-22 or alendronate. The graphs indicate the number of mature OCs identified as positive to TRAP staining and expressed as the number of OCs per visual field at the end of the culture. *=p<0.05.

Figure 8:
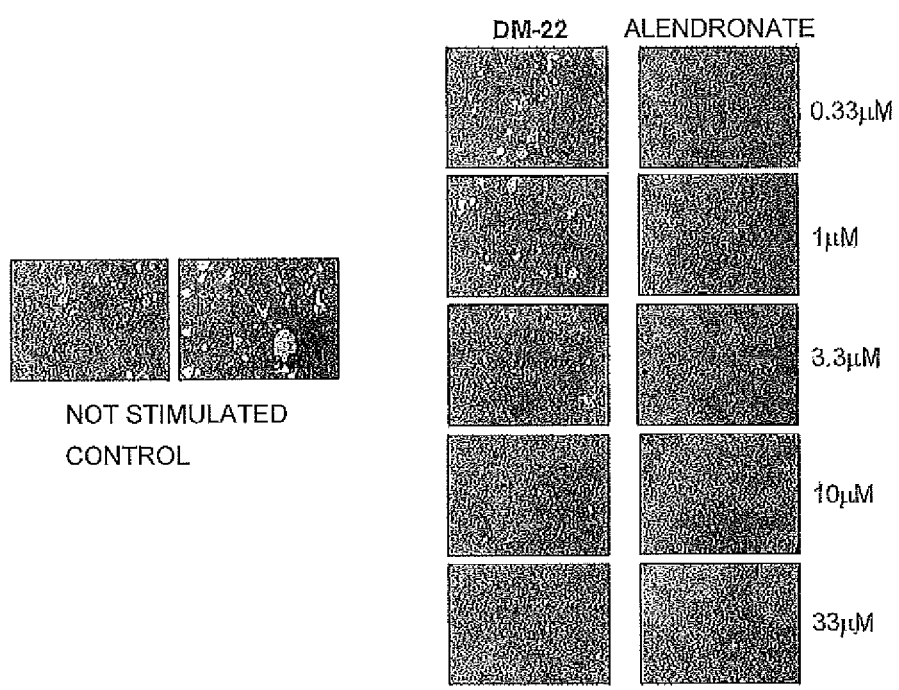
FIG. 8 shows the results of a functional assay of the OCs; one may note images representing the erosion produced by mature OCs on a substrate consisting of an inorganic mineral matrix similar to that making up bone tissue; the white areas represent pits and are thus representative of the erosive activity of OCs.

On completion of the analysis carried out on the OCs, we wanted to verify the data on cellular differentiation with cell function assays. In this assay, called the 'pit assay', the erosive capacity of the OCs is evaluated by making these cells differentiate on a mineral substrate that mimics the composition of the bone mineral matrix. FIG. 8 shows a qualitative evaluation which reveals a behaviour consistent with the outcome of the differentiation assay: alendronate inhibits the erosive capacity of OCs starting from the lowest concentration, whereas in the case of DM-22 the process of inhibition is more gradual and only at the concentrations of 10 and 33 µM do the eroded areas disappear completely. Considered overall, these results suggest that the anti-catabolic effect of alendronate is maintained in DM-22, albeit in an attenuated form, such as to require higher concentrations.

FIG. 8 shows the results of an OC functionality assay. The figure shows images representing the erosion produced by mature OCs on a substrate consisting of an inorganic mineral matrix, similar to that of which bone tissue is composed. The white areas represent the pits and are thus representative of the erosive activity of the OCs.

Discussion of the Results and Conclusions

The present report illustrates the effects in vitro on human bone cells of an innovative molecule of original conception called DM-22. With this molecule the authors sought to combine the osteoanabolic effects of $H_2S$ already observed in numerous preliminary experiments conducted in the laboratory of the Rizzoli Institute, such as the anti-catabolic effects of alendronate, one of the molecules most used in the pharmacology of erosive bone pathologies. In recent years this drug, despite enjoying enormous commercial success, has shown some negative side effects, essentially ascribable to an excessive suppression of the cellular functionality of OCs and osteoblasts alike.

The synthesis of this molecule aims to meet the most pressing needs in pre-clinical research on this type of pathologies: to develop new molecules capable of combining an anti-catabolic effect with one of an anabolic type, in such a way as to favour, rather than suppress, the physiology regulating normal bone turnover.

The results presented make it possible first of all to trace a positive profile of DM-22 from a toxicity standpoint. In the tested range of concentrations, DM-22 demonstrates to be a more cytoprotective and in any case non-toxic molecule compared to the native molecule alendronate, which, by contrast, in agreement with the data in the literature and clinical evidence, tends to induce cell death in MSCs.

As regards the data related to the modulation of cellular functionality, DM-22 has first of all demonstrated to be capable of promoting the ability of MSC cells to deposit mineral matrix; this assay predicts the ability of cells in vivo to perform an osteoanabolic function in bone tissue. The results show an outcome of great relevance, given that not only does DM-22 provide better results than alendronate in each of the tested concentrations, but it also shows, in absolute terms, an induction of the deposition of bone matrix by MSC cells, as compared to control cells induced to osteogenic differentiation.

The potential pharmacological impact of the data on MSC cells is even further reinforced by the data obtained on OCs, which were analysed in order to verify the anticatabolic effects of the compounds of the invention. They show, in fact, that DM-22 preserves its ability to inhibit OC differentiation and function, a property typical of alendronate, but attenuates the effectiveness thereof, making higher dosages necessary in order to reach a similar level of inhibition. In consideration of the fact that alendronate has a very long half-life and shows a marked tendency to accumulate in bone mineral matrix, the data on DM-22 suggest overall that this molecule may have a much more balanced effect than alendronate on bone cells; on the one hand, in fact, DM-22 remains capable in any case of blocking OC function, but as it requires a greater concentration, it could exert a moderate rather than radical suppression of OC function. On the other hand, DM-22 is able to induce, in the same range of concentrations in which it inhibits OCs, a significant function of stimulating mineralisation by human MSCs.

In summary, we believe that the new molecule DM-22 possesses the following unexpected and innovative properties:

DM-22 is a molecule with an original and innovative chemical structure.

DM-22 is capable of liberating $H_2S$ with slow-release kinetics.

Concentrations being equal, DM-22 shows no cytotoxicity and is cytoprotective compared to the 'mother' molecule alendronate. Furthermore, within the limit of 24 h of culture, it is cytoprotective also in absolute terms compared to the unstimulated control.

DM-22 does not modify the proliferative capacity of MSCs, whereas alendronate provokes a marked decrease.

DM-22 is a molecule capable of inducing a significant increase in mineralisation in human osteoprogenitor cells, thus exerting an osteoanabolic function.

In the same range of concentration in which it stimulates the anabolic function (10-33 µM), DM-22 significantly inhibits the differentiation and bone degradation function of osteoclasts.

Concentrations being equal, DM-22 is approximately 33-100 times less effective than alendronate in suppressing OCs, thus suggesting an effect of moderate suppression which maintains the homeostatic function of the OCs themselves intact without causing the total inhibition typical of alendronate.

The invention claimed is:

1. A compound of formula (I) or pharmaceutically acceptable salt thereof:

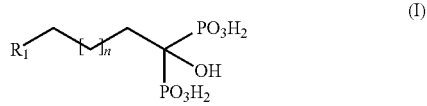

wherein $R_1$ is an RCONH— group, wherein R is an aromatic benzene ring substituted with an SCN— group in the ortho, meta or para position, according, to the following formula:

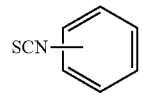

and n can be equal to 0 or 1.

2. The compound of formula (I) according to claim 1, wherein the substitution of the SCN— group is in the para position.

3. The compound according to claim 1, wherein R is a benzene ring ortho-, meta- or para-substituted with an SCN—group and n is equal to 1.

4. The compound of formula (I) according to claim 3, wherein R is a benzene ring para-substituted with an SCN— group and n is equal to 1.

5. The compound of formula (I) according to claim 1 corresponding to (1-hydroxy-4-{[(4-phenyl isothiocyanate) carbonyl]amino}butane-1,1-bisphosphonic acid, according to the following structural formula:

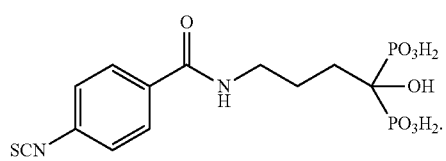

6. Method of treating osteoporosis in patients in need thereof with a medicament comprising the compound of formula (I) or a pharmaceutically acceptable salt thereof according to claim 1, said method comprising administering an effective dose of said compound of formula (I) or of said pharmaceutically acceptable salt thereof to said patients; and treating said osteoporosis.

7. Method of treating rheumatoid arthritis, hyperparathyroidism or bone tumour metastasis in patients in need thereof with a medicament comprising the compound of formula (I) or a pharmaceutically acceptable salt thereof according to claim 1, said method comprising administering an effective dose of said compound of formula (I) or of said pharmaceutically acceptable salt thereof to said patients; and treating said rheumatoid arthritis, hyperparathyroidism or bone tumour metastases.

* * * * *